US012102340B2

(12) United States Patent
Santangelo et al.

(10) Patent No.: US 12,102,340 B2
(45) Date of Patent: Oct. 1, 2024

(54) SURGICAL DRILL GUIDE SYSTEMS AND METHODS OF USE THEREOF

(71) Applicant: Smith & Nephew, Inc., Memphis, TN (US)

(72) Inventors: Stephen Santangelo, Sturbridge, MA (US); Anthony O'Leary, Walpole, MA (US); Matthew Dennis Cunningham, Lakeville, MA (US); Scott Faucett, Washington, DC (US); Jeffrey Wyman, Naples, FL (US); Chun Liu, Brookline, MA (US); Roman Gutierrez, Brighton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 329 days.

(21) Appl. No.: 17/687,228

(22) Filed: Mar. 4, 2022

(65) Prior Publication Data

US 2022/0240954 A1 Aug. 4, 2022

Related U.S. Application Data

(63) Continuation of application No. 16/423,483, filed on May 28, 2019, now Pat. No. 11,298,143, which is a continuation-in-part of application No. PCT/US2018/021111, filed on May 6, 2018.

(60) Provisional application No. 62/484,514, filed on Apr. 12, 2017, provisional application No. 62/677,717, filed on May 30, 2018.

(51) Int. Cl.
*A61B 17/17* (2006.01)
*A61B 50/33* (2016.01)
*A61B 17/00* (2006.01)
*A61B 17/02* (2006.01)
*A61B 17/56* (2006.01)
*A61B 17/90* (2006.01)
*A61B 90/00* (2016.01)

(52) U.S. Cl.
CPC ...... *A61B 17/1764* (2013.01); *A61B 17/1717* (2013.01); *A61B 50/33* (2016.02); *A61B 2017/0042* (2013.01); *A61B 17/02* (2013.01); *A61B 2017/564* (2013.01); *A61B 17/90* (2021.08); *A61B 2090/062* (2016.02)

(58) Field of Classification Search
CPC ..... A61B 50/33; A61B 17/17; A61B 17/1697; A61B 17/1764; A61B 17/1796
See application file for complete search history.

(56) References Cited

U.S. PATENT DOCUMENTS

| | | | |
|---|---|---|---|
| 6,193,724 B1 * | 2/2001 | Chan | A61B 17/175 606/53 |
| 6,241,734 B1 * | 6/2001 | Scribner | A61F 2/4601 606/93 |
| 2004/0073227 A1 * | 4/2004 | Dreyfuss | A61B 17/1778 606/96 |

(Continued)

*Primary Examiner* — David W Bates
(74) *Attorney, Agent, or Firm* — ArentFox Schiff LLP; Joseph M. Maraia; Marlo Schepper Grolnic

(57) ABSTRACT

Surgical drill guides have modular configurations and are adapted to accommodate a wide range of anatomy. The surgical drill guides are adapted to be removed while leaving a guide wire in its intended location in human bone. The distal end of the drill guide acts as a safety stop for the guide wire by preventing the guide wire from penetrating too far past the far side of the bone.

18 Claims, 14 Drawing Sheets

(56) References Cited

U.S. PATENT DOCUMENTS

| | | | | |
|---|---|---|---|---|
| 2008/0097453 A1* | 4/2008 | Stone | ................ | A61B 17/1714 |
| | | | | 606/96 |
| 2010/0256645 A1* | 10/2010 | Zajac | ................ | A61B 17/1764 |
| | | | | 606/80 |
| 2017/0245869 A1* | 8/2017 | Mirochinik | ........ | A61B 17/1617 |

* cited by examiner

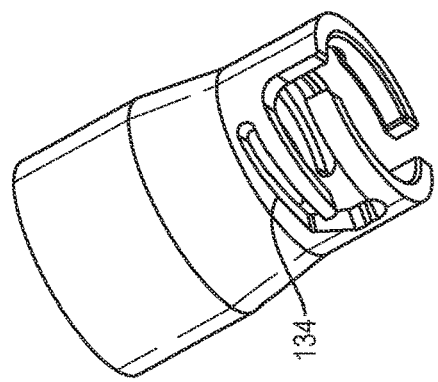
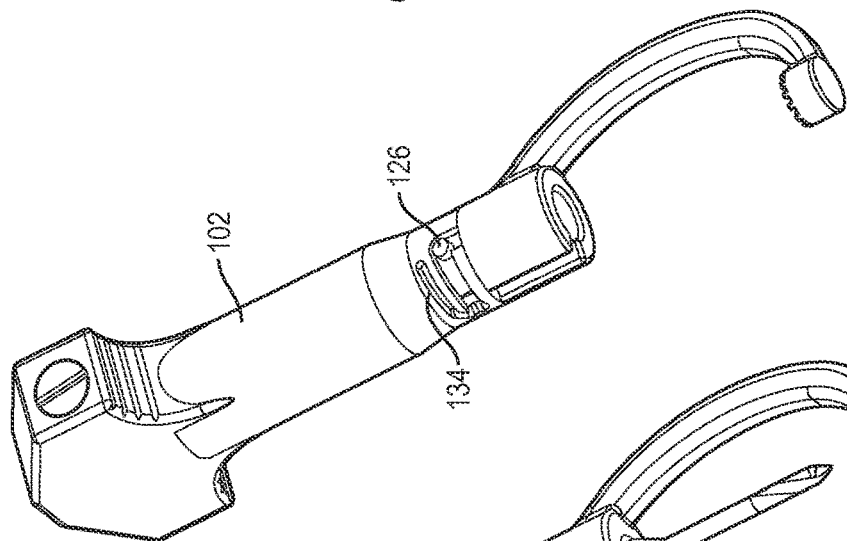
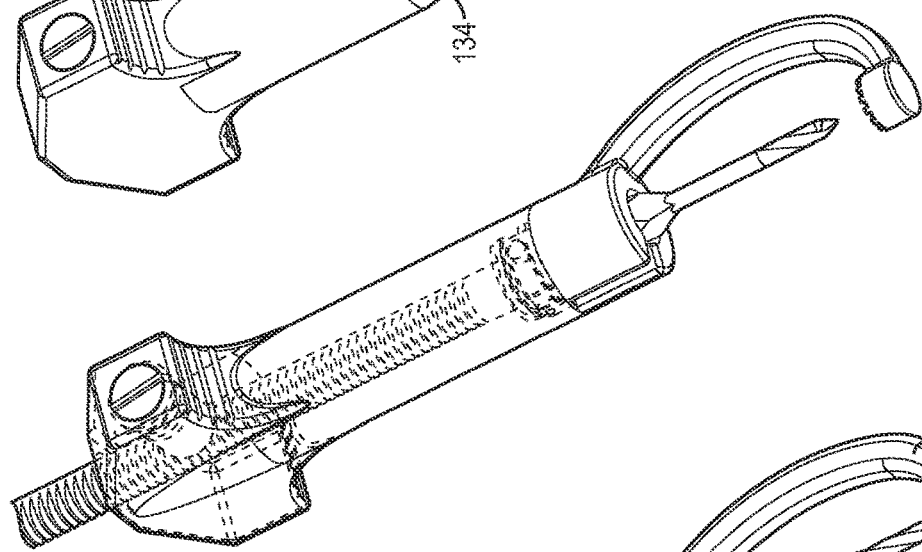
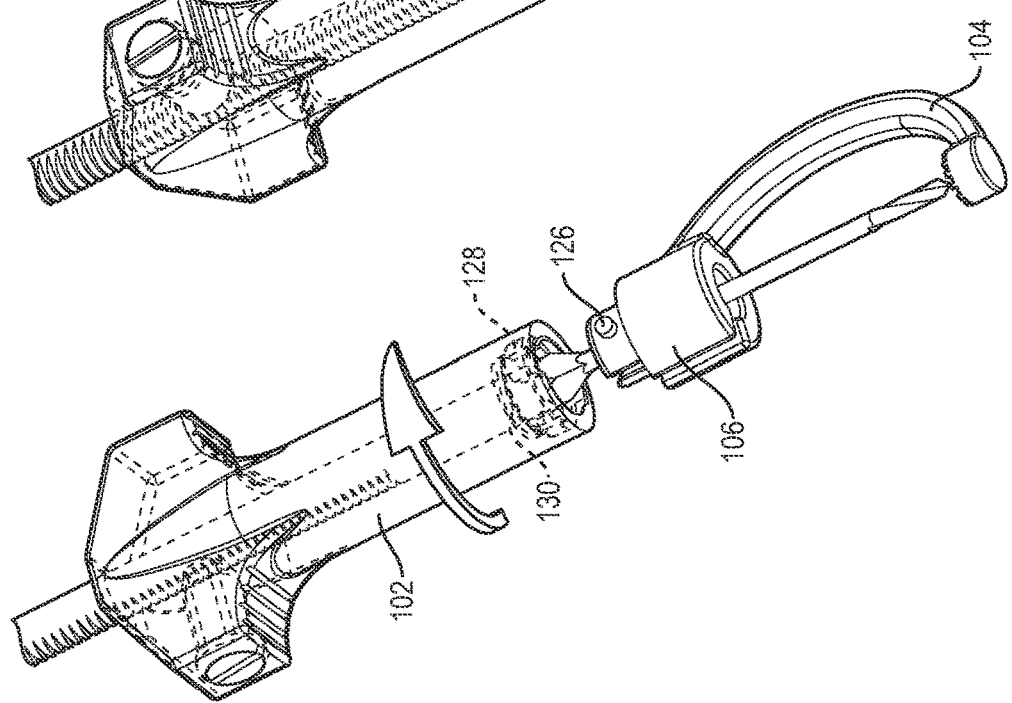

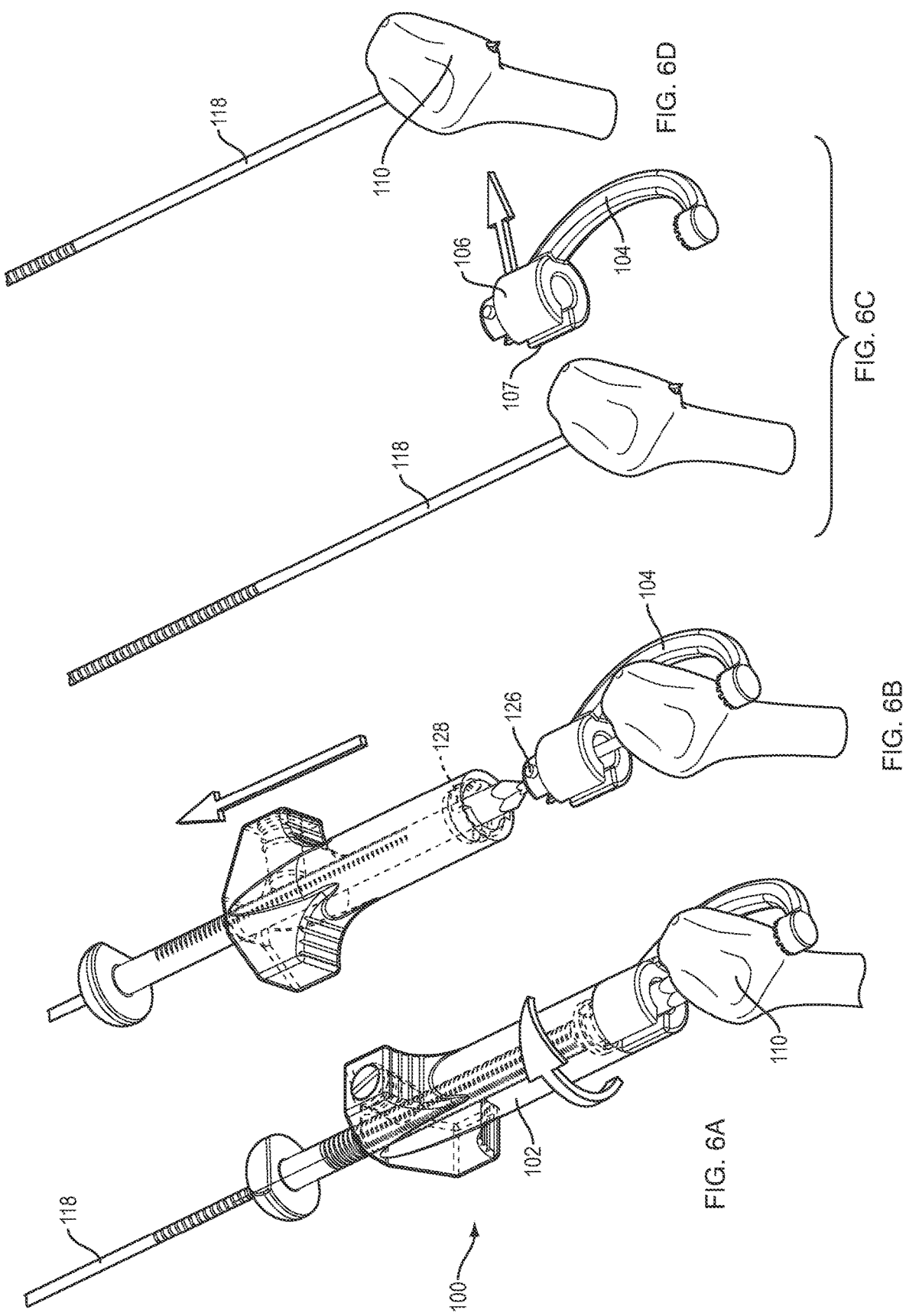

SURGICAL DRILL GUIDE SYSTEMS AND METHODS OF USE THEREOF

CROSS-REFERENCE TO RELATED APPLICATIONS

This application is a continuation of co-pending U.S. application Ser. No. 16/423,483, filed May 28, 2019, entitled SURGICAL DRILL GUIDE SYSTEMS AND METHODS OF USE THEREOF, which in turn is a continuation-in-part of International Application No. PCT/US2018/021111, filed Mar. 6, 2018, entitled SURGICAL DRILL GUIDE SYSTEMS AND METHODS OF USE THEREOF, which in turn claims priority to and benefit of U.S. Provisional Application No. 62/484,514, filed Apr. 12, 2017. U.S. application Ser. No. 16/423,483 also claims priority to and benefit of U.S. Provisional Application No. 62/677,717, filed May 30, 2018 entitled SURGICAL DRILL GUIDE SYSTEMS AND METHODS OF USE THEREOF. The entire contents of the above applications are incorporated herein by reference for all purposes.

FIELD

The present disclosure relates generally to surgical drill guides. More specifically, the present disclosure relates to surgical drill guides used in arthroscopic surgical procedures.

BACKGROUND

Reconstructive bone and ligament surgery often involves drilling into bones to attach soft tissue such as ligaments or tendon grafts, as well as various artificial replacements and/or attachments for articulated joints. Many surgical drill guides are known in the art which are adapted to insert a guide wire into the bone at a predetermined position. The guide wire, after insertion, provides a guide for a cannulated drill by which a passageway is then formed in the bone. The ligament graft or other soft tissue may then be secured in the passageway by a fixation means, such as an interference screw or a suture tied to a screw post.

Many surgical drill guides known in the art have a circular geometry, and may include interchangeable guide arms. The interchangeable guide arms typically have different sized templates for identifying a drill path of the guide wire through the bone. However, these drill guides rely on a fixed radial distance from the handle to the template, while varying a throat length between the handle and the guide arm to place the template at a selected location on bone. Thus, due to both their size and the space required for maneuverability, these drill guides can usually only be used on a large bone, such as a human femur. This can be problematic for the user when a drill guided is need to drill through smaller bones, such as a fibula or tibia.

SUMMARY

Disclosed herein are a surgical drill guides which address the limitations of surgical drill guides known in the art. In one example, the surgical drill guide of this disclosure has a modular, rather than circular, configuration, which allows for a larger number of interchangeable guide arms to be quickly and easily connected to a single handle. The interchangeable guide arms have a contoured geometry and are affixed to the handle by means of a quick disconnect, such as a bayonet fitting. Alternatively, the surgical drill guide has a single-piece handle incorporating the guide arm into the handle, which eliminates the need for the end user to assemble the guide prior to use. In both designs, the distal end of the guide arm acts as a safety stop for the guide wire by preventing the guide wire from penetrating too far past the far side of the bone. Thus, the surgical drill guides of this disclosure have the ability to accommodate a wider range of anatomy, from small fibulas to large femurs. Furthermore, the surgical drill guides of this disclosure have ergonomically balanced designs that allow the drill guide to be removed from the repair site while leaving a guide wire in its intended location in human bone.

Further examples of the surgical drill guide of this disclosure may include one or more of the following, in any suitable combination.

In examples, the surgical drill guide of this disclosure includes an elongate handle having a proximal end, a distal end, and a longitudinal axis extending therebetween. An internal cannulation extends a length of the handle between the proximal end and the distal end. A sleeve member configured to slideably extend through the cannulation has an internal channel for passage of a guide wire and defines an insertion axis. A guide arm is removeably coupled to the distal end of the handle. The guide arm has a proximal portion rotatable relative to the handle, and a distal arcuate portion terminating in a stop disposed at a point along the insertion axis. A tip of the sleeve member and the stop of the guide arm define a drilling path therebetween for the guide wire along the insertion axis.

In further examples, a surface of the sleeve member includes a plurality of grooves for selective engagement with a ratcheting member extending into an interior of the handle. The ratcheting member selectively engages under spring force into each one of the plurality of grooves such that the sleeve member can be advanced progressively until resisted by bone. The proximal portion of the guide arm includes at least one radial pin member for engaging at least one slot in the distal end of the handle. In examples, the at least one slot is an "L" shaped slot or an "S" shaped slot. The proximal portion of the guide arm includes a slot for passage of the guide wire when the guide arm is removed from the guide wire. The tip of the sleeve member is configured to penetrate soft tissue. A guide wire extends through the internal channel of the sleeve member. A surface of the guide wire has a plurality of depth markings to indicate a tunnel length when the guide wire is drilled into bone. A surface of the guide stop has a cup for receiving a distal end of the guide wire. The sleeve member is extendable along the insertion axis through a range between the proximal portion of the guide arm and the stop of the guide arm.

In other examples, the surgical drill guide of this disclosure includes a handle having a proximal portion, a curved distal portion, and an internal cannulation extending through the proximal portion in communication with an exterior of the handle through a slot formed through the proximal portion. A sleeve member configured to slideably extend through the cannulation has an internal channel for passage of a guide wire and defines an insertion axis. The distal portion of the handle terminates in a stop disposed at a point along the insertion axis. A tip of the sleeve member and the stop define a drilling path therebetween for the guide wire along the insertion axis. In examples, a surface of the sleeve member includes a plurality of grooves for selective engagement with a ratcheting member extending into an interior of the handle. The ratcheting member selectively engages under spring force into each one of the plurality of grooves such that the sleeve member can be advanced progressively until resisted by bone. The tip of the sleeve member is configured to penetrate soft tissue. The sleeve member is extendable along the insertion axis through a range between the proximal portion of the handle and the stop on the distal portion of the handle.

In examples, a method for surgical drilling of this disclosure includes: 1) positioning a stop of a drill guide at a placement point on bone along an insertion axis defined by a sleeve member of the drill guide, the sleeve member slideably extending through a handle of the drill guide, the placement point representative of a drilling site on the bone along the insertion axis; 2) advancing a tip of the sleeve member to the drilling site; 3) passing a guide wire through the sleeve member; and 4) drilling the guide wire into the bone along the insertion axis to indicate a path for a surgical drill. In examples, the method further includes removing the drill guide from the guide wire by passing the guide wire through a slot extending through the drill guide. Advancing a tip of the sleeve member to the drilling site includes selectively engaging a ratcheting member extending into an interior of the handle with a plurality of grooves on a surface of the sleeve member. In examples, the method further includes unlocking the ratcheting member by rotating the sleeve to disengage the ratcheting member from the plurality of grooves. In examples, the method further includes using a plurality of markings on a surface of the guide wire to measure an insertion depth of the guide wire in the bone.

In examples, a surgical kit of this disclosure includes at least one surgical drill guide system and at least one sleeve configured for use with the at least one surgical drill guide system. In examples, the kit also includes one of an offset guide, a retractor, and/or a tray. The at least one surgical drill guide system includes an elongate handle having a proximal end, a distal end, and a longitudinal axis extending therebetween, with an internal cannulation extending a length of the handle between the proximal end and the distal end. The surgical drill guide system also includes a sleeve member configured to slideably extend through the cannulation having an internal channel for passage of a guide wire and defining an insertion axis, and a guide arm removeably coupled to the distal end of the handle. The guide arm has a proximal portion rotatable relative to the handle, and a distal arcuate portion terminating in a stop disposed at a point along the insertion axis. A tip of the sleeve member and the stop of the guide arm define a drilling path therebetween for the guide wire along the insertion axis. In further examples, the at least one drill guide comprises at least one of a fibular drill guide, a tibial drill guide, and a femoral drill guide.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIGS. 3A-C illustrate a connection system of the surgical drill guide of FIG. 2A and method of use;

FIGS. 4A, 4B and 5 illustrate alternative connection systems of the surgical drill guide of FIG. 2A;

FIGS. 6A-D illustrate a method of removing the surgical drill guide of FIG. 2A from a surgical repair site;

DETAILED DESCRIPTION

Figure 1:
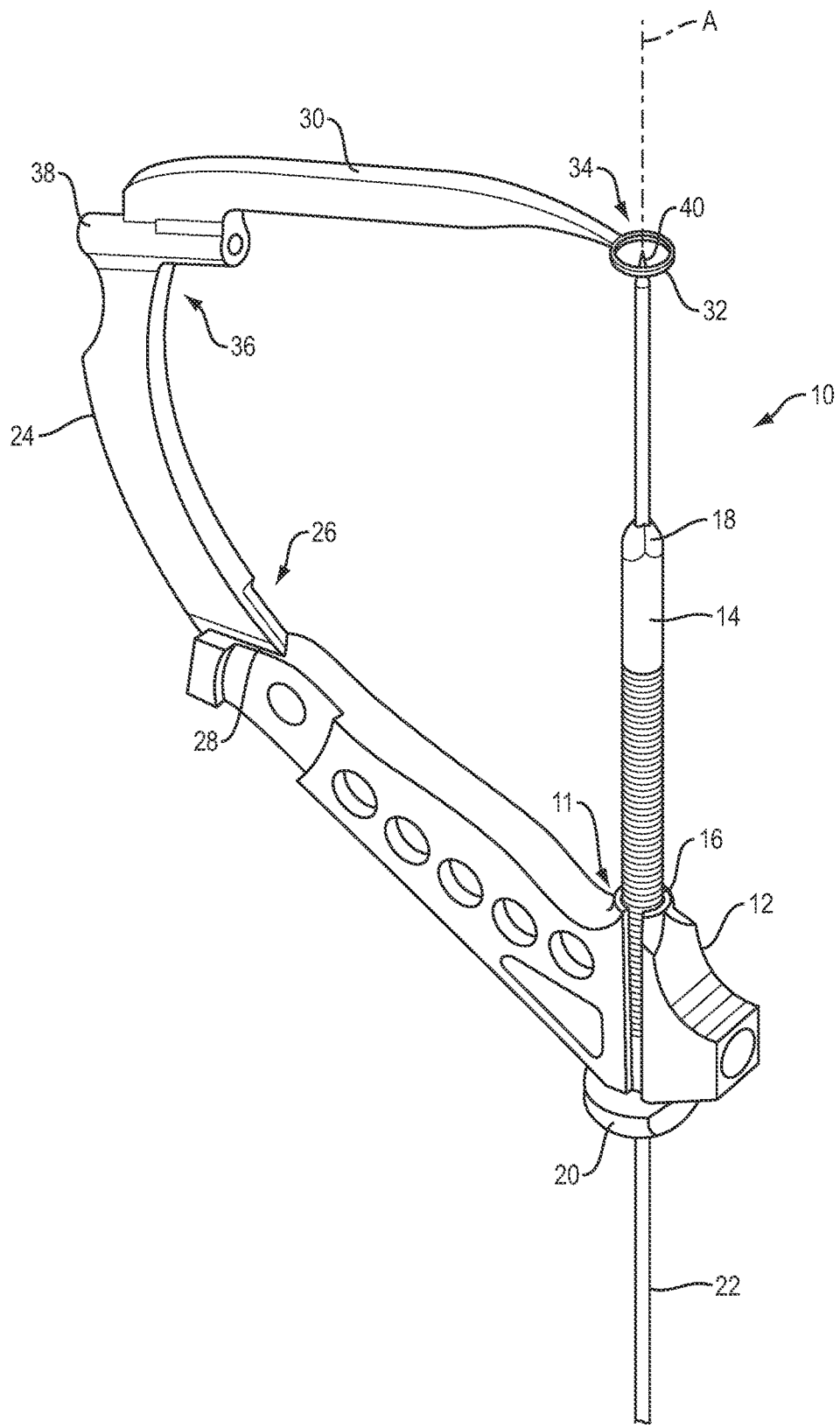
FIG. 1 illustrates a prior art surgical drill guide.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Referring now to FIG. 1, an exemplary prior art surgical drill guide 10 is shown for comparison to the surgical drill guide of this disclosure. In FIG. 1, the surgical drill guide 10 includes a handle or housing 12 having a sleeve 14 disposed through an aperture 16 in the proximal end 11 of the housing 12. The sleeve 14, sometimes known in the art as a "bullet," has a tip 18 and an insertion knob 20 for directing a guide wire 22 to an insertion point on a bone, such as a human femur (not shown). An aimer arm 24 slideably couples to the housing 12 at a distal end 26 of the housing 12 via a slot 28 in the housing 12, and may have an arc shape for arcuate movement thereto. A guide arm 30 having a template 32 at the distal end 34 of the guide arm 30 couples to a distal end 36 of the aimer arm 24. The guide arm 30 may have a hinge 38 connected to the aimer arm 24 for rotation of the guide arm 30 and the template 32 in the plane defined by the guide arm 30 and the sleeve 14. The guide arm 30 may or may not be interchangeable with other guide arms 30 having different sized templates 32 for forming different diameters of the bone tunnel. For example, the guide arm 30 may be releaseably attached to the hinge 38 via a screw extending through the hinge 48 and a threaded portion of the guide arm 30 (not shown). The template 32 which is placed on the farther side of the bone to be drilled, includes an aperture 40 providing an indication of the diameter and the location of the resulting bone tunnel. The sleeve 14 defines an insertion axis (A) indicating the path of the bone tunnel through the bone towards the template 32. As can be seen in FIG. 1, because of its size and the space required to situate the template 32 at a suitable location on bone, the surgical drill guide 10 can generally only be used on large human bones.

Figure 2A:
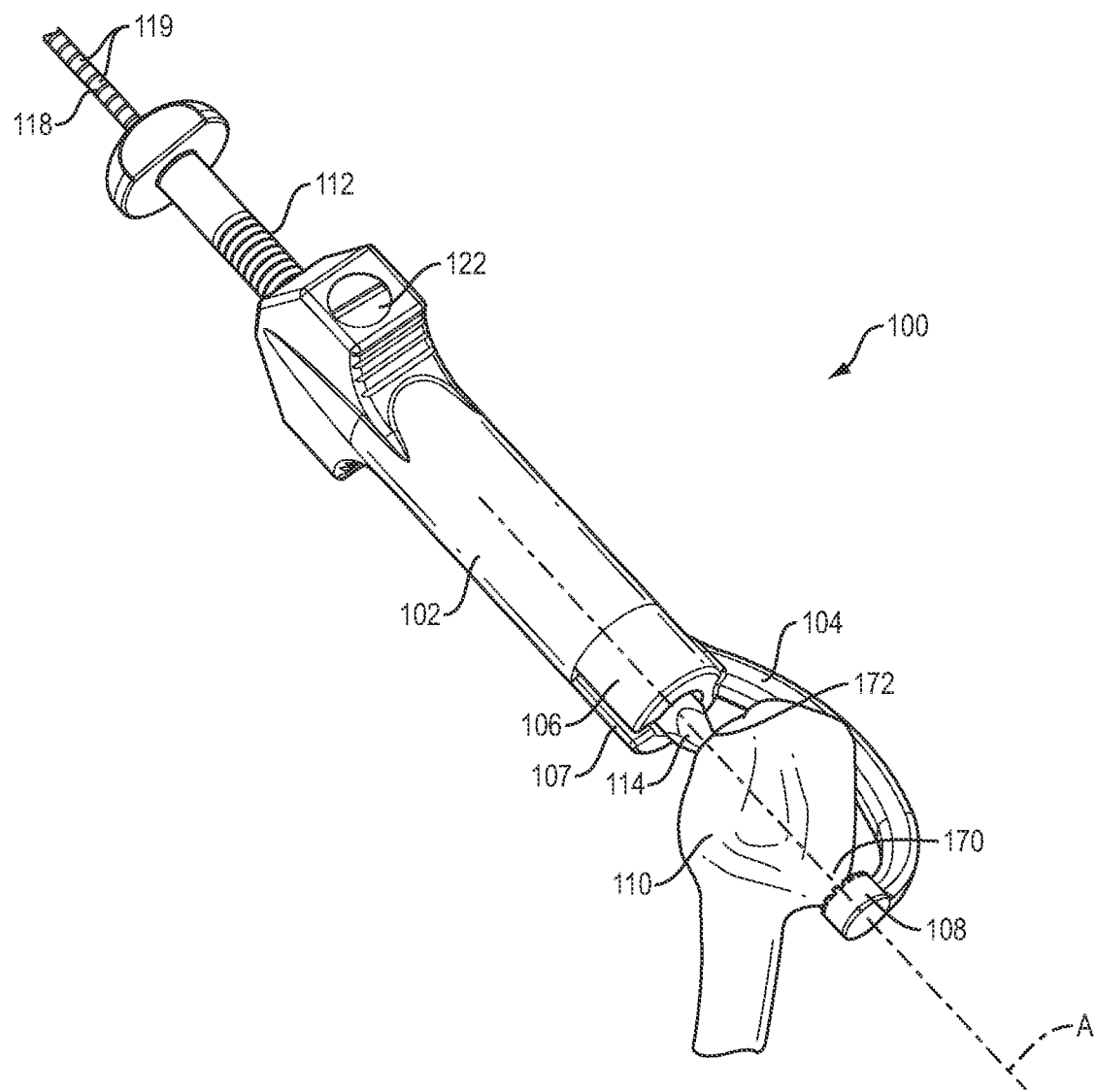
FIG. 2A is a perspective view of a first example of a surgical drill guide of this disclosure and method of use.

Turning now to FIG. 2A, an exemplary surgical drill guide 100 of this disclosure is shown. In general, the surgical drill guide 100 of this disclosure is sized and shaped to navigate a bone 110 to allow correct alignment for generating a bone tunnel along an insertion axis (A) in the bone 110 via a guide wire 118, which may be a drill-tipped guide wire, as further described below. As shown in FIG. 2A, the surgical drill guide 100 includes a cannulated, generally tubular handle 102. A distal end of the handle 102 is coupled to a guide adaptor 106, which is configured to secure an arcuate guide arm 104 to the handle 102, as further described below. The guide adaptor 106 includes a linear slot 107 for disengaging the guide arm 104 from the guide wire 118. The guide arm 104 also includes a guide stop 108 formed at the distal end of guide arm 104 for limiting travel of the guide wire 118 along the insertion axis (A). A hollow sleeve 112 is disposed through the handle 102 for passage of the guide wire 118. A taper, serration, or other suitable engaging edge on the tip 114 of the sleeve 112 facilitates the fixing of the sleeve 112 against the bone 110. In other examples, not shown, the sleeve 112 can be in the form of a cannulated screw with a rotating trocar head. A surface of the guide wire 118 includes depth markings 119 for measuring the tunnel length while drilling the guide wire 118 into the bone 110. The guide stop 108 may further include one or more projections, such as teeth 138 (as shown in FIG. 2A), to provide a secure fit to the bone 110.

Figure 2B:
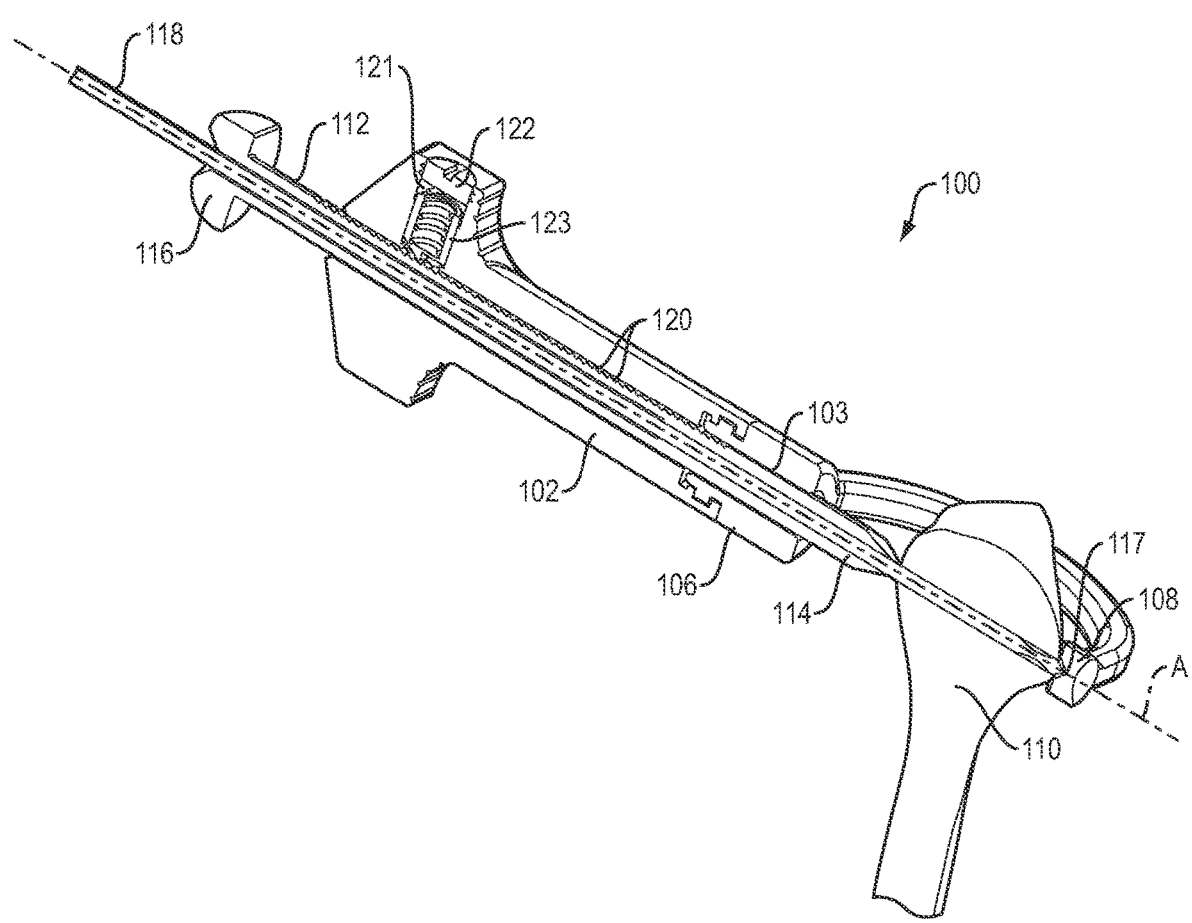
FIG. 2B is a cross-sectional view of the surgical drill guide of FIG. 2A.

Turning now to FIG. 2B, the surgical drill guide 100 is shown in a cross-sectional view. As can be seen in FIG. 2B, the sleeve 112 is adapted for slideable movement within a cannulation 103 of the handle 102 along the insertion axis (A). The sleeve 112 is extendable along the insertion axis (A) through a range between the guide adaptor 106 and the guide stop 108 to define a drilling and/or insertion cup for the guide wire 118. A surface of the sleeve 112 includes a plurality of profiled grooves 120 for selective engagement with a lock 123 of a ratcheting member 122 disposed within a channel 121 defined by the handle 102 in communication with the cannulation 103.

Figure 2C:
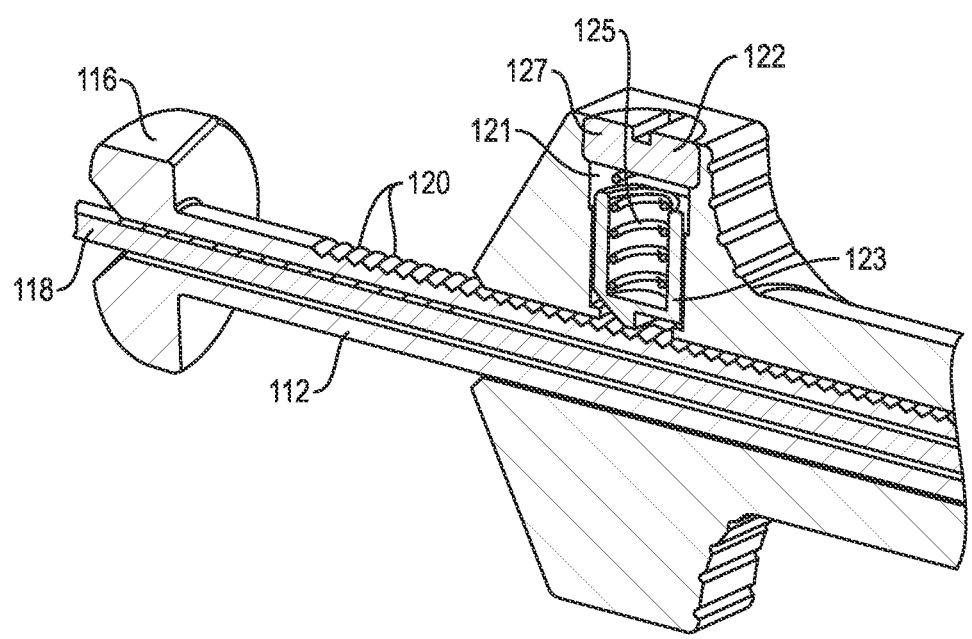
FIG. 2C is a detailed view of the ratcheting member of FIG. 2B.

As shown in FIG. 2C, the ratcheting member 122 also includes a spring 125 disposed within the lock 123, and a retainer 127. The lock 123 engages under spring force into each groove 120 of the sleeve 112 such that the sleeve 112 can be advanced progressively until resisted by the bone 110. The ratcheting member 122 can be unlocked from the sleeve 112 by rotating the sleeve 112 via an insertion knob 116 about 90 degrees, for example, in a counter-clockwise direction, to disengage the lock 123 from the grooves 120. Typically, an incision is made where the tip 114 of the sleeve 112 contacts soft tissue (not shown), and the sleeve 112 is advanced until the bone 110 is encountered. The tip 114 engages the bone 110 facilitated by the ratcheting member 122 to avoid slippage during insertion of the guide wire 118.

A bone-facing surface of the guide stop 108 furthermore comprises a cup 117 for receiving the distal end of the guide wire 118 (FIG. 2B).

Figure 3A:
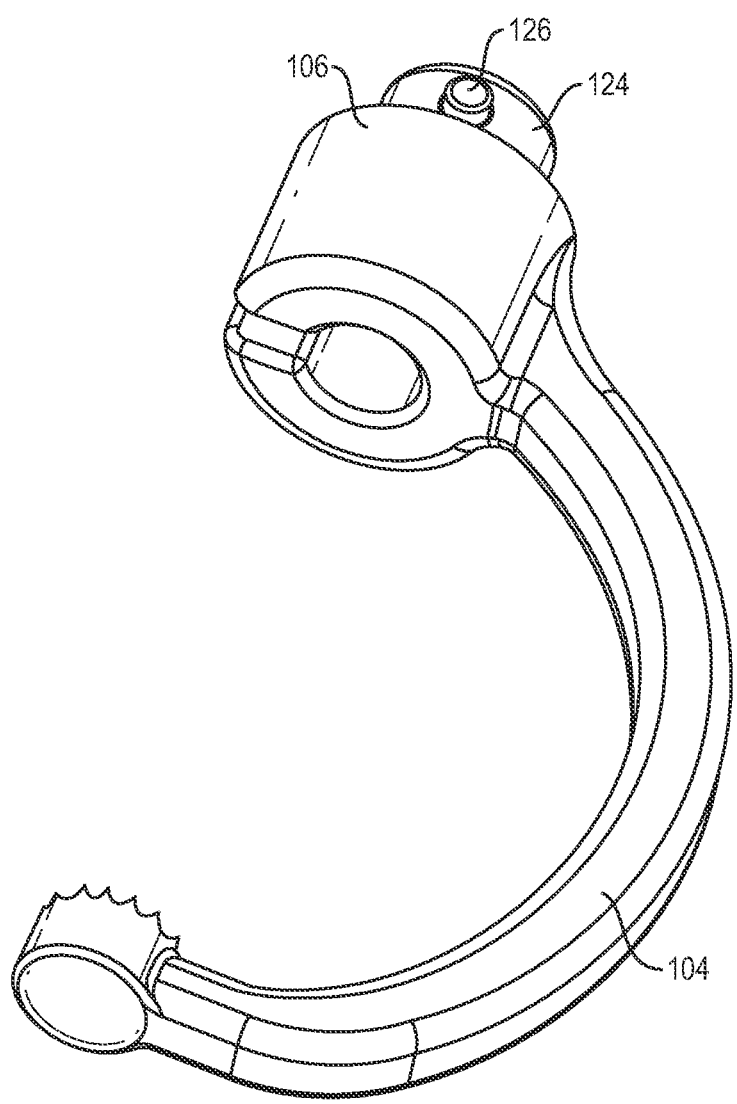

FIGS. 3A-C illustrate an example of a connection system for attaching the guide adaptor 106 of the guide arm 104 to the distal end of the handle 102. As shown in FIG. 3A, unlike the threaded screw connections of prior art systems, the connection of this disclosure is in the form of a quick and simple "bayonet" connection wherein the guide adaptor 106 has a cylinder 124 at the proximal end of the guide adaptor 106. The cylinder 124 includes at least one radial pin 126. As shown in FIG. 3B, the pin 126 is configured for releasable engagement with at least one corresponding "L" shaped slot 128 in the distal end of the handle 102 when the handle 102 is rotated, for example, in a clockwise direction. This slot 128 allows the pin 126 to rotationally slide the guide adaptor 106 into a locked position, as illustrated in FIG. 3C. Within the handle 102, moreover, is a spring element 130 which applies a constant holding force on the pin 126. When the pin 126 is rotated into the locked position, the spring element 130 aids in keeping the pin 126 positioned within the recess of the slot 128, thus preventing the pin 126 from accidentally rotating free. Thus, the connection system of this disclosure allows for easy and quick interchangeability of various sized and contoured aimer guides 104 that can accommodate different sized bones in a surgical procedure, as compared with more complicated threaded connections.

Figure 5:
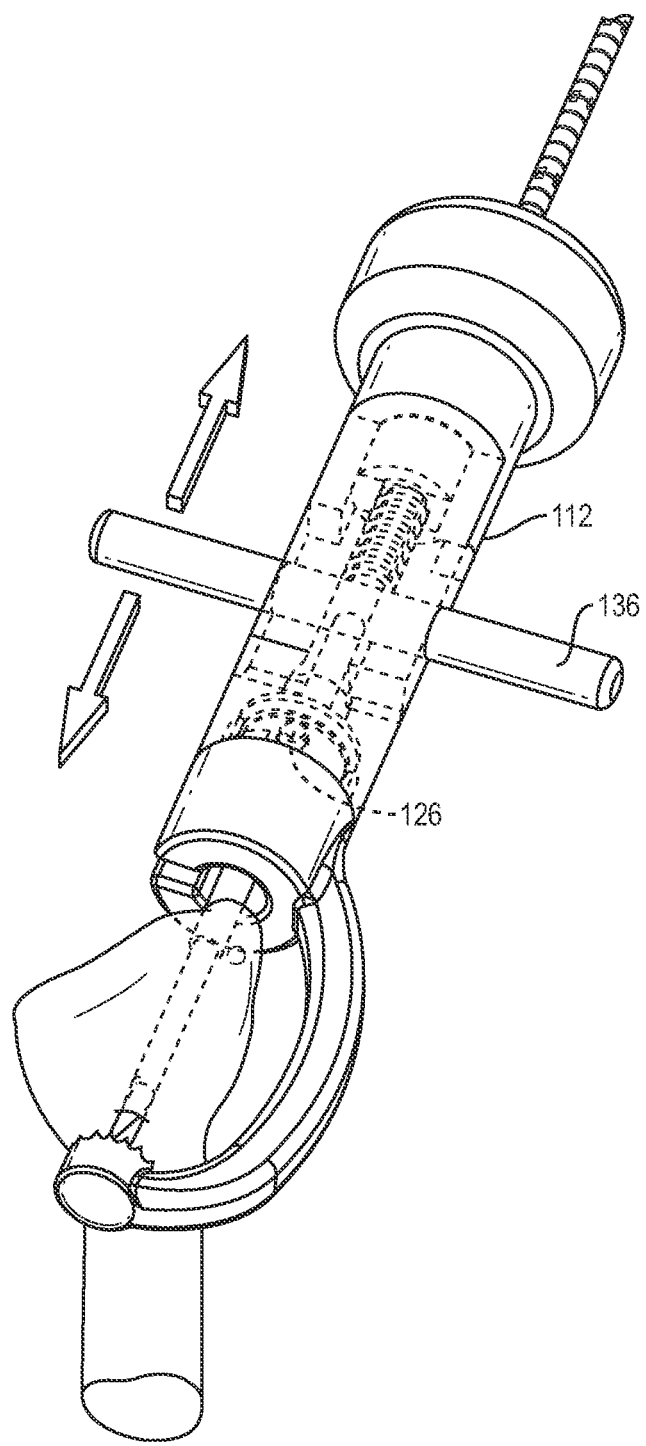

An alternative example of a connection system is shown in FIGS. 4A and 4B. In FIGS. 4A and 4B, the connection is a "living hinge" connection formed by an "S" shaped slot 134 in the distal end of the handle 102. The slot 134 allows the pin 126 to rotationally slide the guide adaptor 106 into a locked position. In another example, illustrated in FIG. 5, the connection system further includes spring-loaded cross handle 136 extending through the sleeve 112. The spring-loaded cross handle 136 provides a continuous holding force on the pin 126. In other examples, not shown, the connection system can be in the form of a quick-disconnect, for example, a spring loaded ball-and groove. The connection system may also be in the form of a multi-start thread.

FIGS. 6A-D illustrate a method of removing the drill guide 100 from the repair site once the guide wire 118 has been set in the correct location in bone 110. As shown in FIGS. 6A and 6B, the handle 102 can be rotated, for example, in a counter-clockwise direction, and moved proximally relative to the guide adaptor 106 to disengage the pin 126 from the slot 128 (or the slot 134 of FIGS. 4A and 4B), and thus to release the handle 102 from the guide arm 104. As illustrated in FIG. 6C, the guide arm 104 is then removed from the guide wire 118 via the slot 107 in the guide adaptor 106. As shown in FIG. 6D, the guide wire 118 remains inside the bone 110, forming the template for the tunnel to be drilled in the bone 110.

Returning now to FIG. 2A, a method of surgical drilling using an exemplary surgical drill guide 100 of this disclosure is further illustrated. FIG. 2A shows the surgical drill guide 100 disposed at a surgical site comprising the bone 110. To begin the method, a surgeon or other operator disposes the guide stop 108 of the guide arm 104 at a placement point 170 on the bone 110. Typically, the placement point 170 would be the same location as the prior attachment point of a ligament being repaired, but other suitable locations may be determined. The surgeon then disposes the sleeve 112 such that the sleeve 112 is slideably movable through the handle 102. The tip 114 of the sleeve 112 is then advanced toward the drilling site 172, such as an anatomically sound location on the bone 110, using the ratcheting mechanism of the ratchet member 122. This allows for the marking and fixing, via the edge at the tip 114 of the sleeve 112, of a drilling site 172 for insertion of the guide wire 118. It is notable that the placement point 170 for the guide stop 108 defines a location along the insertion axis (A) for insertion of the guide wire 118 towards the drilling site 172. By advancing the sleeve 112, the tip 114 of the sleeve 112 passes through soft tissue (not shown) and contacts the drilling site 172 at the bone, cartilage, or other hard surface underneath the soft tissue. A cannulated drill (not shown) may subsequently be employed to further excavate a tunnel from the drilling site 172 towards the placement point 170 of the guide stop 108.

Figure 7A:
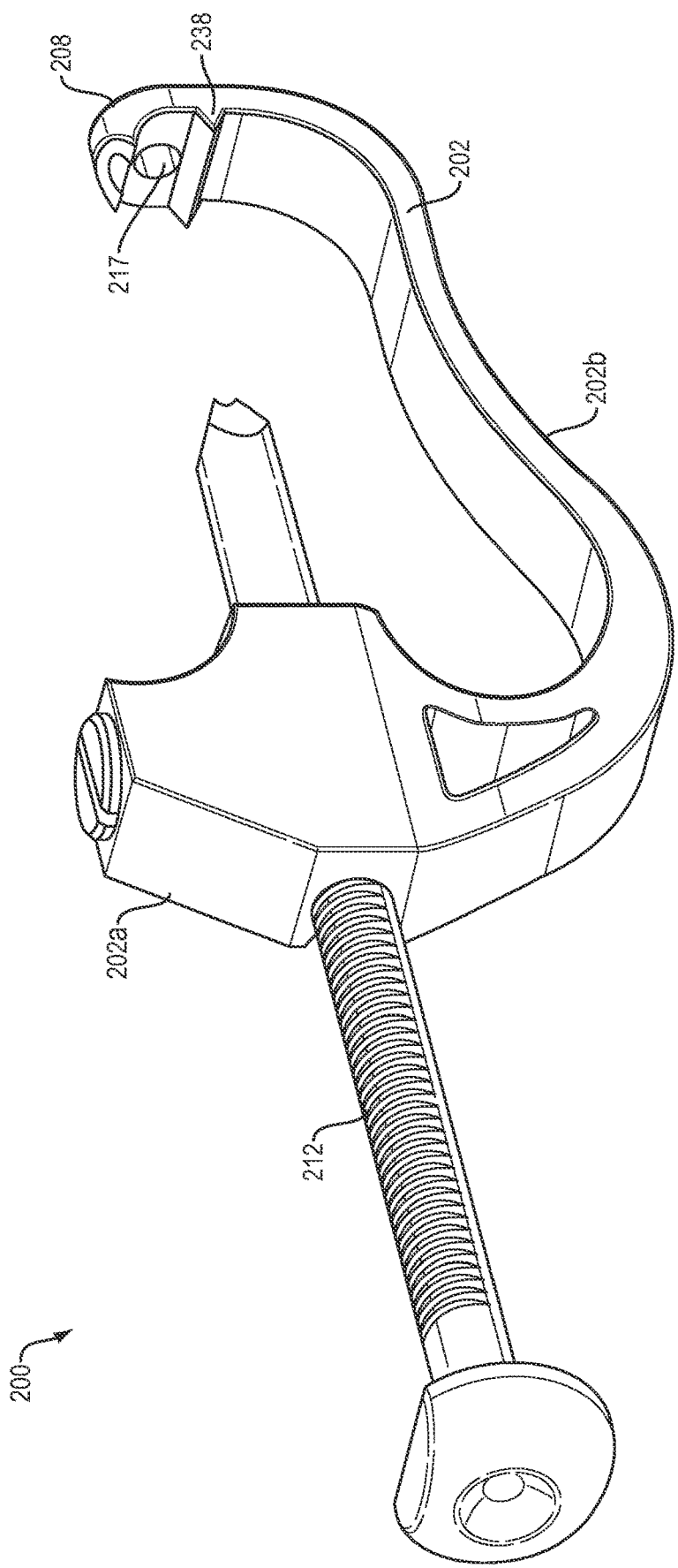
FIG. 7A illustrates a second example of a fibular drill guide of this disclosure.

FIG. 7A illustrates an alternative example of a surgical drill guide, such as a fibular drill guide 200, which aims to simplify the use and assembly for the end user. The fibular drill guide 200 is similar to the drill guide 100 in configuration and use except as described below. In general, the fibular drill guide 200 has a single-piece handle 202 and an accompanying sleeve 212. The handle 202 comprises a proximal portion 202a and a curved distal portion 202b. The handle 202 also includes a guide stop 208 formed at the distal terminus of the distal portion 202b. The guide stop 208 may include one or more cleats 238 (e.g., four, as shown) to provide a secure fit to the bone, and a cup 217 for receiving the distal end of the guide wire.

Figure 7B:
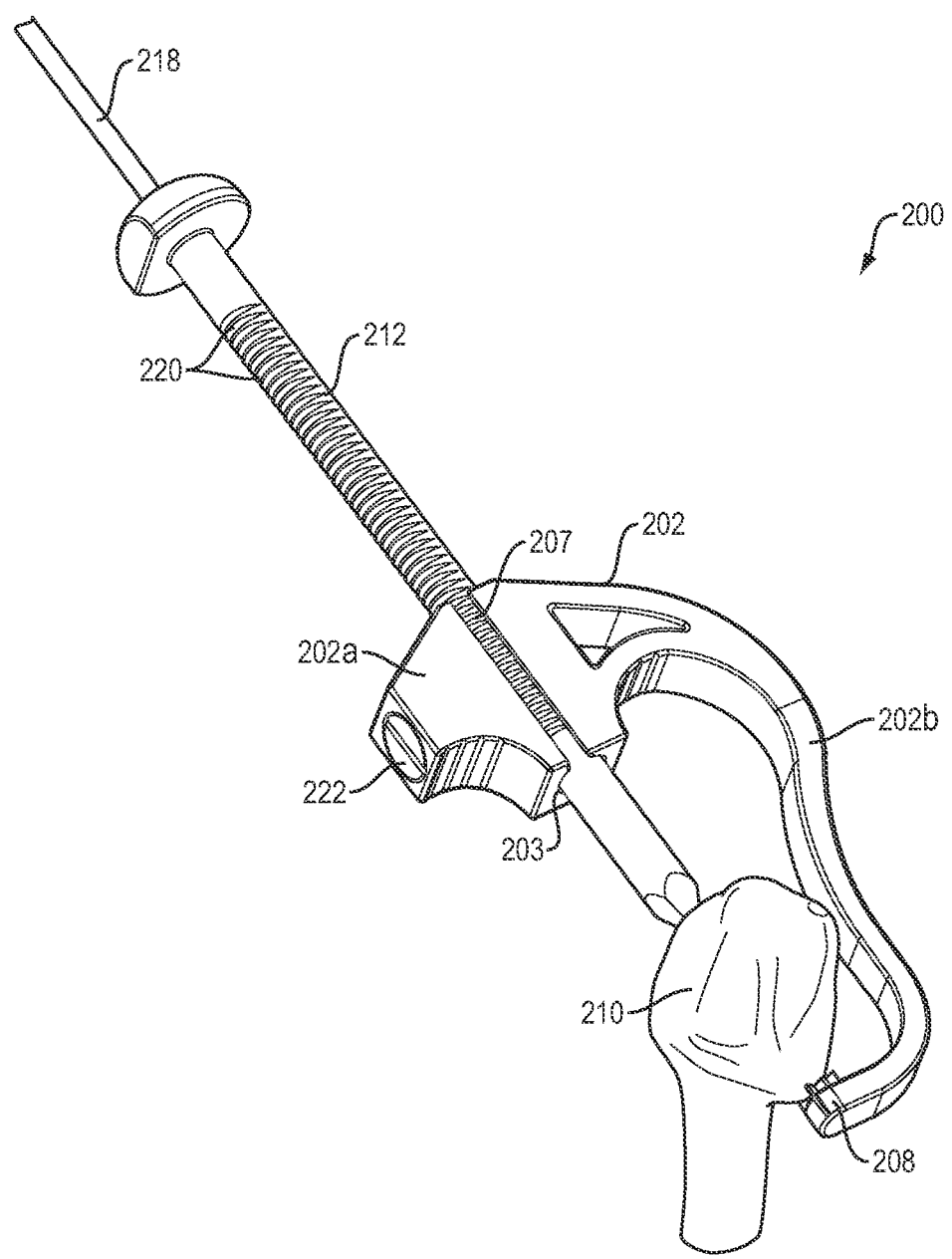
FIGS. 7B-E illustrate a method of using the fibular drill guide of FIG. 7A.

As shown in FIG. 7B, the proximal portion 202a of the handle 202 includes an internal cannulation 203 for passage of the sleeve 212 in communication with an exterior of the handle 202 through a slot 207 formed in the proximal portion 202a of the handle 202. The proximal portion 202a also includes a self-locking ratcheting member 222, which is similar to ratcheting member 122 described above. The ratcheting member 222 interacts with the sleeve 212 as the sleeve 212 is advanced through the cannulation 203, assuming that the grooves 220 in the sleeve 212 are aligned with the ratcheting member 222. Once the sleeve 212 is ratcheted down along the insertion axis (A) to secure the fibular drill guide 200 onto the bone 210, a guide wire 218 is used to drill across the bone 210. Upon drilling through both sides of the bone 210, the tip of the guide wire 218 will contact the guide stop 208 of the distal portion 202b of the handle 202, preventing further drilling and protecting the surrounding soft tissue.

Figure 7E:
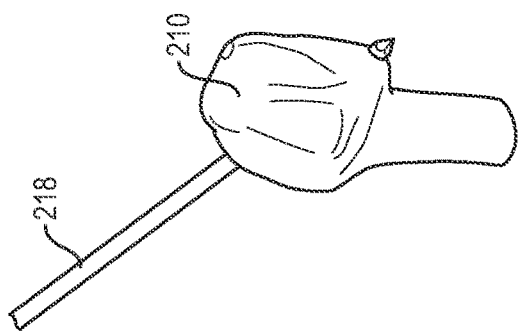
Figure 7D:
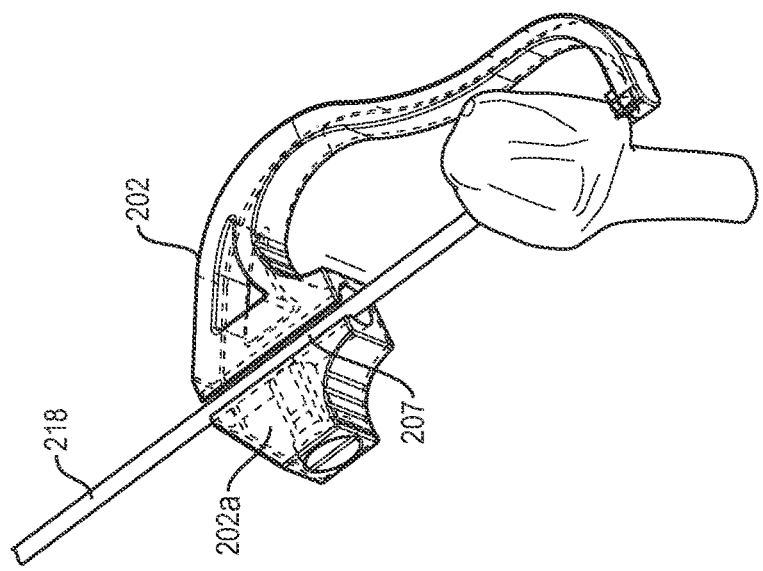
Figure 7C:
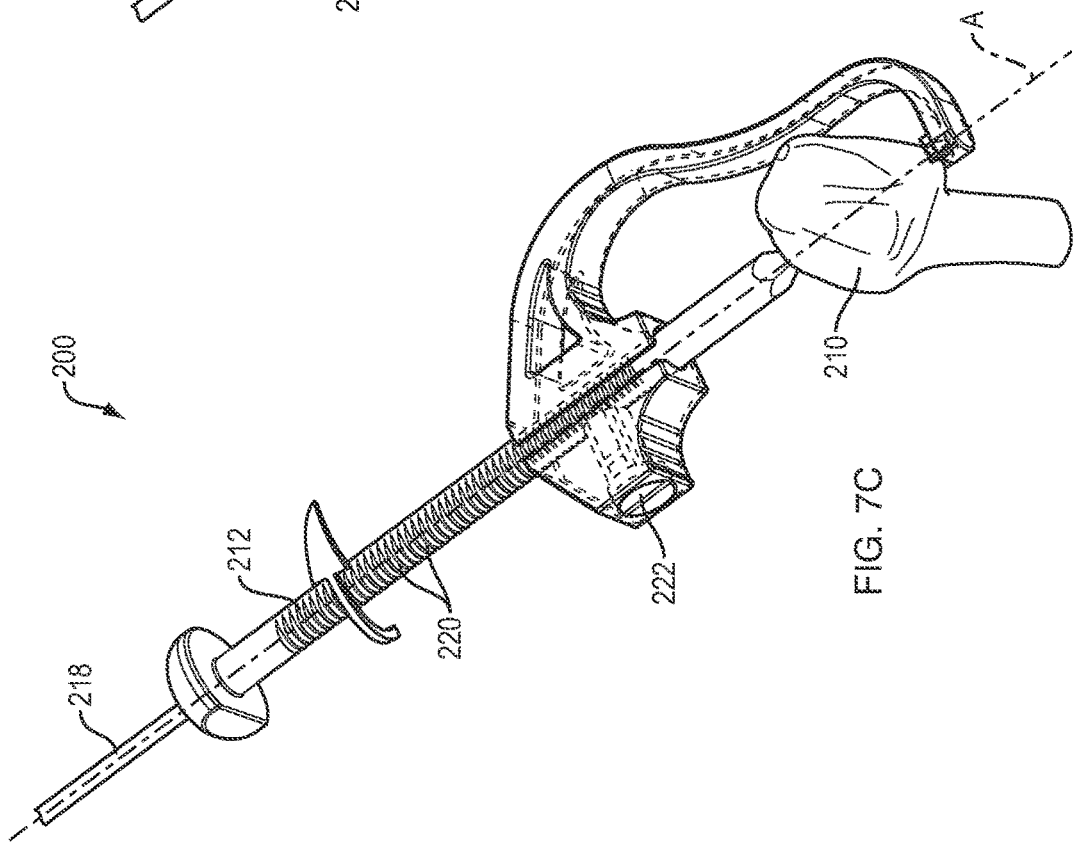

FIGS. 7C-E illustrate the removal of the fibular drill guide 200 from the repair site once the guide wire 218 has been placed in bone 210. First, as shown in FIG. 7C, the sleeve 212 is rotated, for example, in a counter-clockwise direction, until the grooves 220 on the sleeve 212 disengage from the ratcheting member 222. Once disengaged, the sleeve 212 is fully retracted from the handle 202 and the guide wire 218, as illustrated in FIG. 7D. Next, utilizing the slot 207 formed through the proximal portion 202a of the handle 202, the fibular drill guide 200 is removed from the guide wire 218, as shown in FIG. 7E. Once removed, only the guide wire 218 remains in the bone 210, which is now ready for over-drilling.

Figure 8:
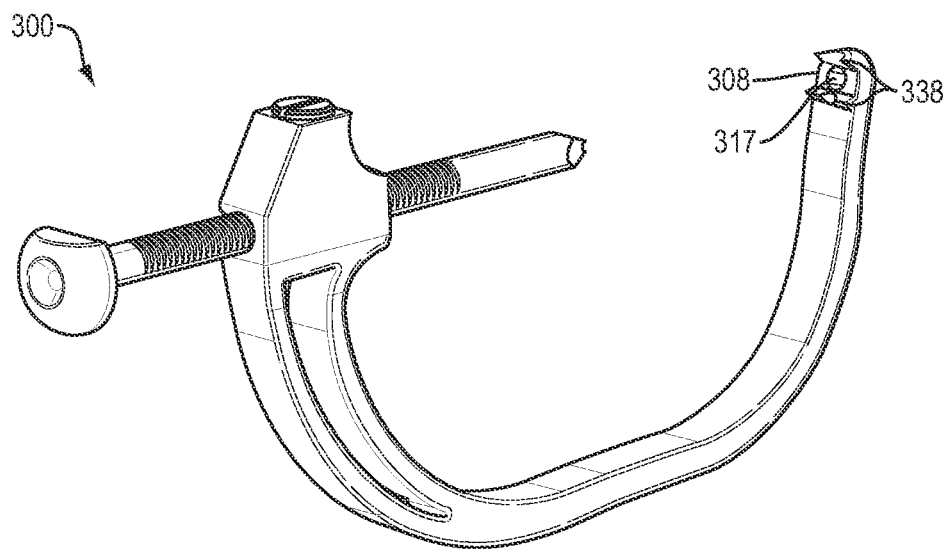
FIG. 8 illustrates a tibial drill guide of this disclosure.
Figure 9:
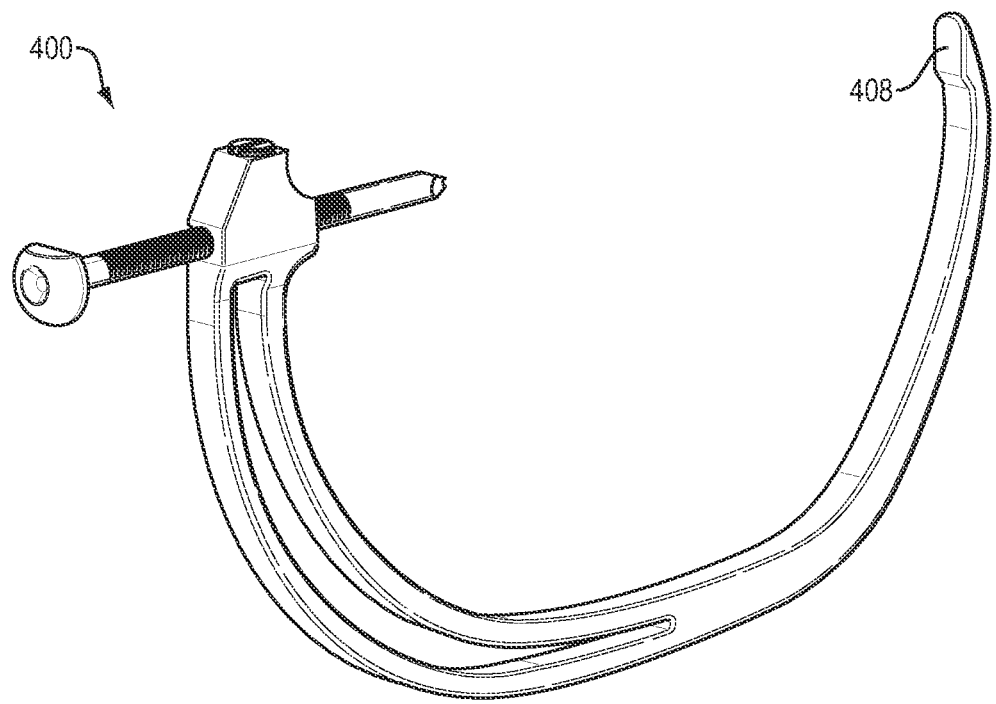
FIG. 9 illustrates a femoral drill guide of this disclosure.

The fibular drill guide 200 may be conveniently sized and shaped for drilling through a fibula. However, a tibial drill guide 300 (FIG. 8) and a femoral drill guide 400 (FIG. 9) may be conveniently sized and shaped for drilling through a tibia and femur, respectively. Notably, while the guides 200, 300, 400 of this disclosure have geometries unique to the soft tissue and bony anatomies corresponding with their intended areas of use, the guide stops 208, 308, 408 of the guides 200, 300, 400 differ with respect to their intended placements. Because the guides 200 and 300 are designed for use within joint spaces and must be anchored onto bone, the guide stops 208, 308 comprise cleats 238, 338 to provide a secure fit to the bone. Additionally, a cup 217, 317 is featured in the guide stops 208, 308 for capturing the tip of the guide wire upon exiting the bone to prevent unintended damage to the surrounding soft tissue and neurovascular structures. In contrast, examples of the guide stop 408 of the femoral drill guide 400 are provided with a flat, atraumatic surface to prevent damage to external soft tissue, since the guide stop 408 must be secured to the thigh.

Figure 10A:
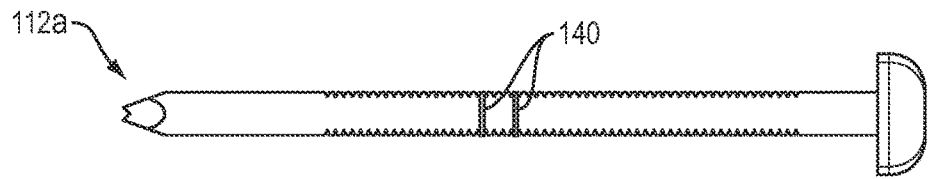
FIGS. 10A and 10B illustrate examples of sleeves for use with the drill guides of this disclosure.
Figure 10B:
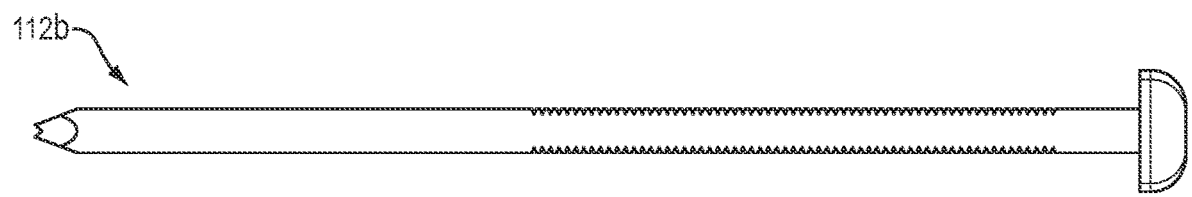

Turning now to FIGS. 10A and 10B, it will be appreciated that the drill guides 200, 300, 400 of this disclosure may be configured for the use with sleeves of a variety of lengths. For example, FIG. 10A illustrates a sleeve 112a which is selected to have a shorter length than the sleeve 112b of FIG. 10B. In examples, a length of the sleeve 112a may be about 4.5 inches, and a length of the sleeve 112b may be about 6.5 inches. The sleeve 112a may be typically used with the fibular drill guide 200, while the sleeve 112b may typically be used with the tibial drill guide 300 and the femoral drill guide 400. In examples, the sleeve 112a comprises two circumferential laser marks 140 that read, for instance, "20 mm" and "25 mm." The laser marks 140 on the sleeve 112a may be used to provide a tunnel length estimation when mated with the fibular drill guide 200, since a minimum tunnel length of 20-25 mm is typically used when drilling in the fibula. In contrast, in the cases of tibial and femoral tunnel drilling, the tunnel lengths are typically of no particular concern. Thus, in examples, the sleeve 112b has no circumferential laser marks.

Figure 11:
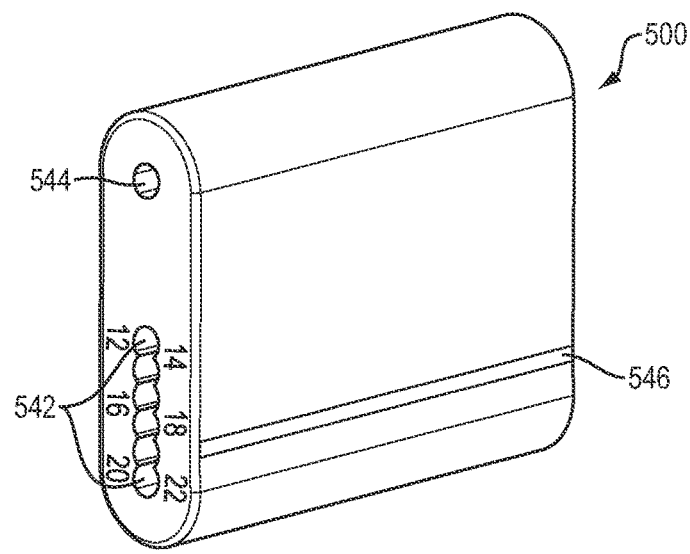
FIG. 11 illustrates an offset guide for use with the drill guides of this disclosure.

At least one of the drill guides 200, 300 and 400 may be provided in a kit along with at least one of the sleeves 112a and 112b of FIGS. 10A and 10B. The kit may furthermore include one or more additional instruments. For example, the kit may include an offset guide, such as the offset guide 500 shown in FIG. 11. The offset guide 500 may provide a means of displacing a secondary guide wire at a set distance from the guide wire 118, 218 initially placed in the bone. This is accomplished through a series of overlapping holes 542 in the offset guide 500 which are incrementally displaced from a standalone hole 544. In examples, the holes 542, 544 are sized to accommodate a 2.4 mm guide wire. A laser line 546 marking the 18 mm hole on the offset guide 500 may be provided for easy visualization of the recommended guide wire displacement.

Figure 12:
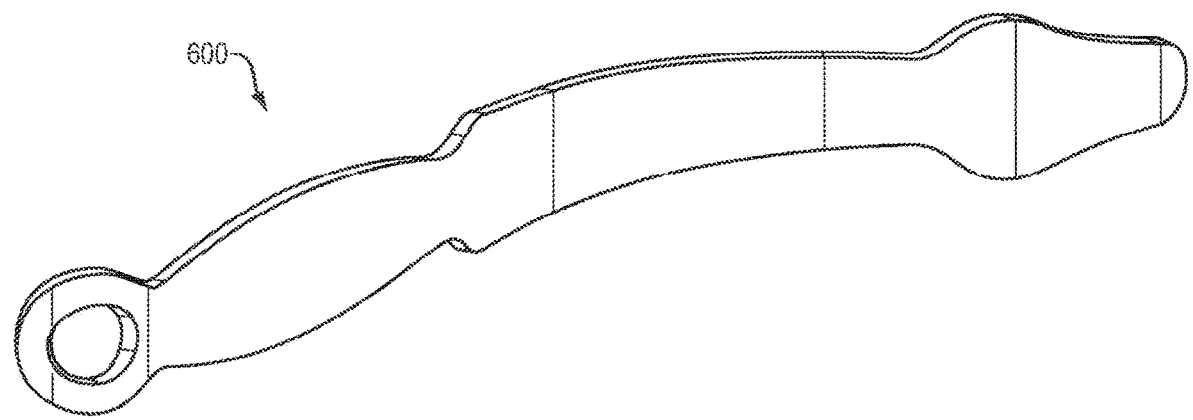
FIG. 12 illustrates a retractor for use with the drill guides of this disclosure.
Figure 13:
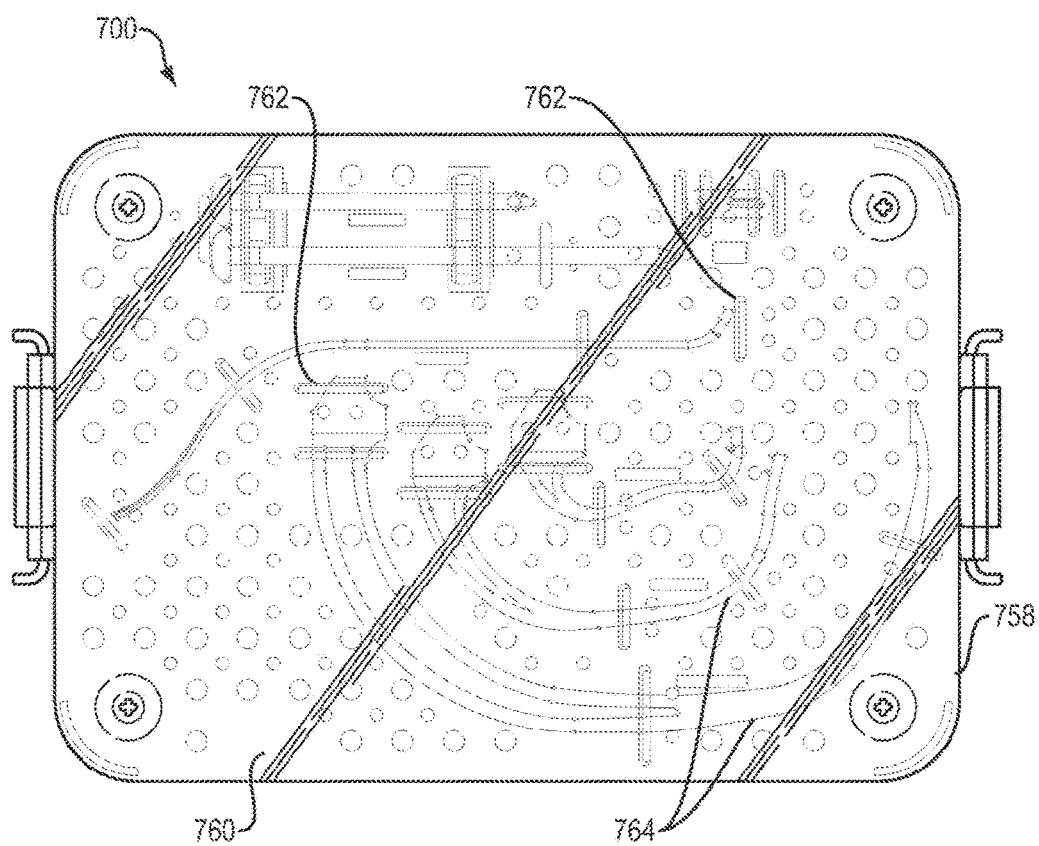
FIG. 13 illustrates an instrument tray for use with the drill guides of this disclosure.

In further examples, the kit may also include a retractor, such as the Chandler retractor 600 shown in FIG. 12, manufactured by Innomed, Inc. (Savannah, GA). The retractor 600 may aid in retracting and protecting sensitive soft tissue and/or nerves in the joint space while drilling the guide wire 118, 218. The retractor 600 may be positioned behind the guide stops 208, 308 of the drill guides 200, 300 while drilling to provide additional protection in cases where the guide wire 118, 218 is not sufficiently captured by the cups 117, 217 due to divergence. A custom instrument tray, such as the tray 700 shown in FIG. 13, may furthermore be provided with the kit to allow for proper steam sterilization and subsequent storage and/or transport of the instruments. In examples, the tray 700 comprises a transparent lid 758 and separate base 760 with nylon-coated brackets 762 installed to secure the instruments within the tray 700. Additionally, the base 760 may contain laser marks 764 with instrument outlines to denote the general placement and orientation of the instruments. It is also contemplated by this disclosure that, as an alternative to the fibular drill guide 200, the tibial drill guide 300 and the femoral drill guide 400, the kit may be provided with a universal handle (such as the handle 102 of FIG. 2A) configured to mate with three different fibular, tibial and femoral arms to address the necessary anatomy. In examples, all of the instruments in the kit are reusable.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

What is claimed is:

1. A surgical drill guide system comprising:
   a single-piece handle having a proximal portion and a curved distal portion, a cannulation extending through the proximal portion, the cannulation in communication with an exterior of the handle through a slot formed through the proximal portion;
   a sleeve member configured to slideably extend through the cannulation, the sleeve member having an internal channel for passage of a guide wire, the sleeve defining an insertion axis; and
   a ratcheting member disposed within a channel defined by the proximal portion of the handle, the channel extending perpendicular to the insertion axis;
   wherein the distal portion of the handle terminates in a stop disposed at a point along the insertion axis;
   wherein a tip of the sleeve member and the stop define a drilling path therebetween for the guide wire along the insertion axis; and
   wherein a surface of the sleeve member comprises a plurality of profiled grooves for selective engagement with a lock of the ratcheting member, a spring disposed within the lock causing the lock to engage the plurality of grooves such that the sleeve member can be advanced progressively until resisted by bone.

2. The surgical drill guide system of claim 1, wherein the tip of the sleeve member is configured to penetrate soft tissue.

3. The surgical drill guide system of claim 1, wherein the sleeve member is extendable along the insertion axis through a range between the proximal portion of the handle and the stop on the distal portion of the handle.

4. The surgical drill guide system of claim 1, wherein the stop comprises a plurality of cleats.

5. The surgical drill guide system of claim 1, wherein the stop comprises a cup for receiving a distal end of the guide wire.

6. The surgical drill guide system of claim 1, wherein the ratcheting member is self-locking.

7. The surgical drill guide system of claim 1, wherein a curved distal portion has an "S" curve.

8. The surgical drill guide system of claim 1, wherein an outer surface of the sleeve comprises indicia for providing tunnel length estimation.

9. The surgical drill guide system of claim 1, wherein the ratcheting member further comprises a retainer.

10. The surgical drill guide system of claim 1, wherein the spring is configured to contact the retainer.

11. A surgical kit comprising:
    at least one surgical drill guide system;
    at least one sleeve member configured for use with the at least one surgical drill guide system;
    an offset guide;
    a retractor; and
    a tray;
    wherein the at least one surgical drill guide system comprises:
      a single-piece handle having a proximal portion and a curved distal portion, a cannulation extending through the proximal portion, the cannulation in communication with an exterior of the handle through a slot formed through the proximal portion;
      a sleeve member configured to slideably extend through the cannulation, the sleeve member having an internal channel for passage of a guide wire, the sleeve defining an insertion axis; and
      a ratcheting member disposed within a channel defined by the proximal portion of the handle, the channel extending perpendicular to the insertion axis;
    wherein the at least one sleeve member is configured to slideably extend through the cannulation, the at least one sleeve member having an internal channel for passage of a guide wire and defining an insertion axis;
    wherein the distal portion of the handle terminates in a stop disposed at a point along the insertion axis;
    wherein a tip of the at least one sleeve member and the stop define a drilling path therebetween for the guide wire along the insertion axis; and
    wherein a surface of the sleeve member comprises a plurality of profiled grooves for selective engagement with a lock of the ratcheting member, a spring disposed within the lock causing the lock to engage the plurality of grooves such that the sleeve member can be advanced progressively until resisted by bone.

12. The kit of claim 11, wherein the at least one surgical drill guide system comprises at least one of a fibular drill guide, a tibial drill guide, and a femoral drill guide.

13. The kit of claim 11, wherein the stop comprises a plurality of cleats.

14. The kit of claim 11, wherein the stop comprises a cup for receiving a distal end of the guide wire.

15. The kit of claim 11, wherein the ratcheting member is self-locking.

16. The kit of claim 11, wherein a curved distal portion has an "S" curve.

17. The kit of claim 11, wherein an outer surface of the sleeve comprises indicia for providing tunnel length estimation.

18. The kit of claim 11, wherein the ratcheting member further comprises a retainer.

* * * * *

UNITED STATES PATENT AND TRADEMARK OFFICE
CERTIFICATE OF CORRECTION

PATENT NO. : 12,102,340 B2
APPLICATION NO. : 17/687228
DATED : October 1, 2024
INVENTOR(S) : Stephen Santangelo et al.

Page 1 of 1

It is certified that error appears in the above-identified patent and that said Letters Patent is hereby corrected as shown below:

On the Title Page

Item (63):
"Continuation of application No. 16/423,483, filed on May 28, 2019, now Pat. No. 11,298,143, which is a continuation-in-part of application No. PCT/US2018/021111, filed on May 6, 2018"

Should read:
--Continuation of application No. 16/423,483, filed on May 28, 2019, now Pat. No. 11,298,143, which is a continuation-in-part of application No. PCT/US2018/021111, filed on March 6, 2018.--

Signed and Sealed this
Twenty-fifth Day of March, 2025

Coke Morgan Stewart
*Acting Director of the United States Patent and Trademark Office*